US009649053B2

(12) United States Patent
DiCesare et al.

(10) Patent No.: US 9,649,053 B2
(45) Date of Patent: *May 16, 2017

(54) CAM-ACTUATED MEDICAL PUNCTURING DEVICE AND METHOD

(71) Applicant: Becton, Dickinson and Company, Franklin Lakes, NJ (US)

(72) Inventors: Paul C. DiCesare, Easton, CT (US); Jeffrey Radziunas, Wallingford, CT (US); Christopher A. Battles, Seymour, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 157 days.

This patent is subject to a terminal disclaimer.

(21) Appl. No.: 14/543,142

(22) Filed: Nov. 17, 2014

(65) Prior Publication Data
US 2015/0073463 A1    Mar. 12, 2015

Related U.S. Application Data

(63) Continuation of application No. 11/568,634, filed as application No. PCT/US2005/015859 on May 5, 2005, now Pat. No. 8,998,941.
(Continued)

(51) Int. Cl.
*A61B 17/32*    (2006.01)
*A61B 5/15*    (2006.01)
*A61B 5/151*    (2006.01)

(52) U.S. Cl.
CPC .......... *A61B 5/1411* (2013.01); *A61B 5/1513* (2013.01); *A61B 5/150022* (2013.01);
(Continued)

(58) Field of Classification Search
CPC ............ A61B 5/1411; A61B 5/150022; A61B 5/150412; A61B 5/150564;
(Continued)

(56) References Cited

U.S. PATENT DOCUMENTS 3,030,959 A    4/1962  Grünert
4,577,630 A    3/1986  Nitzsche et al.
(Continued)

FOREIGN PATENT DOCUMENTS

JP    61-286738 A    12/1986
JP    2003-502088 T    1/2003
WO    03049613    6/2003

*Primary Examiner* — Ashley Fishback
(74) *Attorney, Agent, or Firm* — The Webb Law Firm

(57) ABSTRACT

The medical puncturing device includes a housing, a shield, and a skin puncturing assembly disposed within the housing. The shield is axially movable in the housing. The skin puncturing assembly includes a movable carrier and a skin puncturing element mounted to the carrier. A distal end of the skin puncturing element is adapted for puncturing the skin of a patient. The carrier is movable from a retracted position wherein the skin puncturing element is disposed within the shield to a puncturing position wherein the distal end of the skin puncturing element is exposed. The carrier is maintained in the retracted position by engagement of flexure members or a retaining tab with the carrier. A drive spring is provided to move the carrier from the retracted position to the puncturing position. A retraction spring is provided to return the carrier and skin puncturing element into the housing.

22 Claims, 10 Drawing Sheets

Related U.S. Application Data

(60) Provisional application No. 60/572,317, filed on May 19, 2004, provisional application No. 60/569,424, filed on May 7, 2004.

(52) U.S. Cl.
CPC ....... *A61B 5/15111* (2013.01); *A61B 5/15117* (2013.01); *A61B 5/15142* (2013.01); *A61B 5/15144* (2013.01); *A61B 5/15186* (2013.01); *A61B 5/150259* (2013.01); *A61B 5/150412* (2013.01); *A61B 5/150442* (2013.01); *A61B 5/150503* (2013.01); *A61B 5/150564* (2013.01); *A61B 5/150618* (2013.01); *A61B 5/150717* (2013.01); *A61B 5/150832* (2013.01); *A61B 5/150885* (2013.01)

(58) Field of Classification Search
CPC ........ A61B 5/150618; A61B 5/150709; A61B 5/150717; A61B 5/150885; A61B 5/15111; A61B 5/15117; A61B 5/15142; A61B 5/15144; A61B 5/15186
See application file for complete search history.

(56) References Cited

U.S. PATENT DOCUMENTS

| | | |
|---|---|---|
| 4,627,445 A | 12/1986 | Garcia et al. |
| 4,637,403 A | 1/1987 | Garcia et al. |
| 4,653,513 A | 3/1987 | Dombrowski |
| 5,540,709 A | 7/1996 | Ramel |
| 5,628,765 A * | 5/1997 | Morita ................ A61B 5/1411 604/136 |
| 5,964,718 A | 10/1999 | Duchon et al. |
| 6,066,103 A | 5/2000 | Duchon et al. |
| 6,248,120 B1 | 6/2001 | Wyszogrodzki |
| 6,432,120 B1 | 8/2002 | Teo |

\* cited by examiner

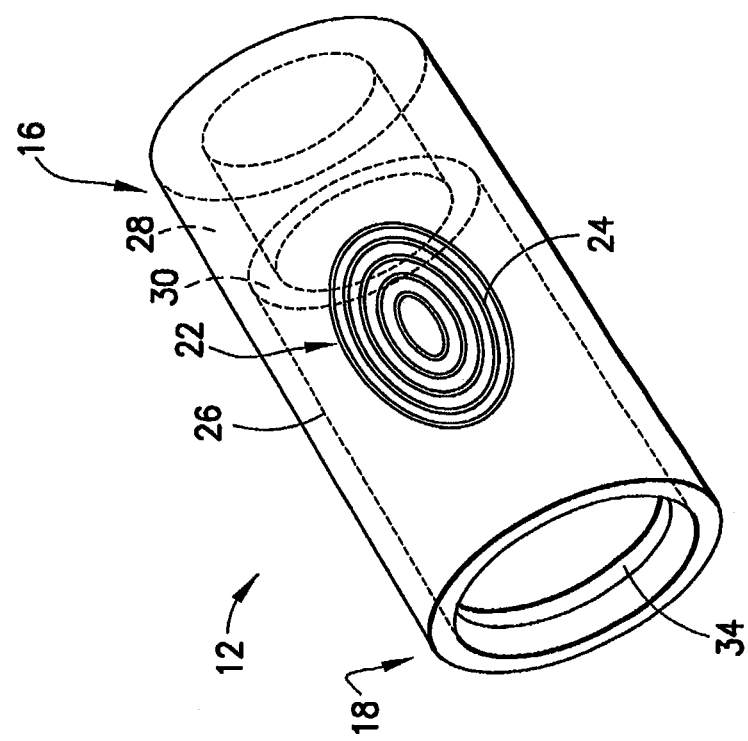

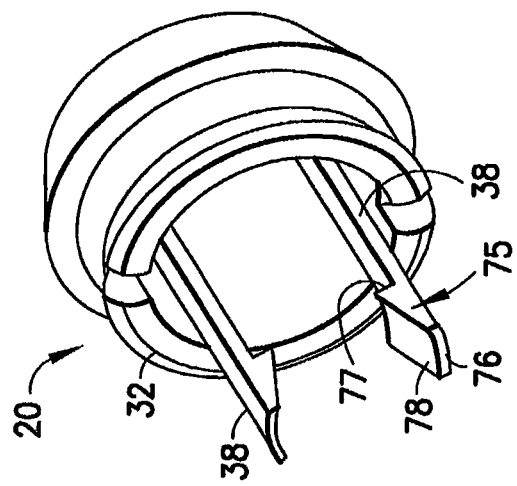
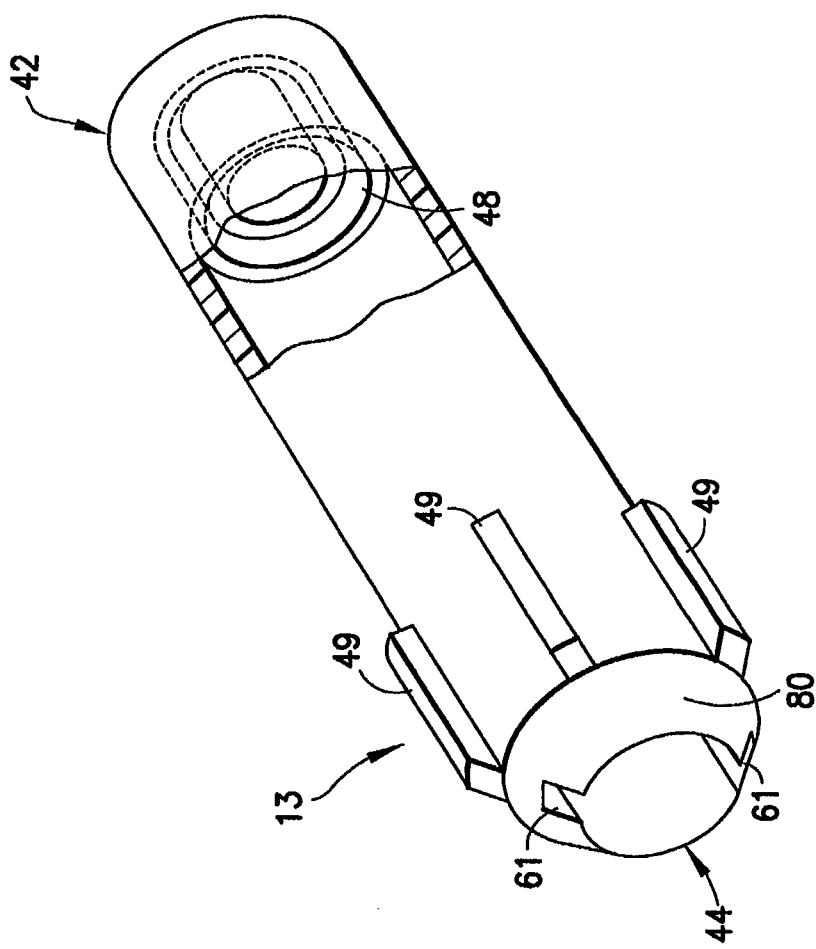

CAM-ACTUATED MEDICAL PUNCTURING DEVICE AND METHOD

CROSS REFERENCE TO RELATED APPLICATIONS

This application is a continuation application of U.S. application Ser. No. 11/568,634, filed Oct. 19, 2007, entitled "Cam-Actuated Medical Puncturing Device and Method", which is a national stage application of International Application No. PCT/US2005/015859, filed May 5, 2005, which claims benefit of U.S. Provisional Patent Application Nos. 60/572,317, filed May 19, 2004, and 60/569,424, filed May 7, 2004, the entire disclosures of each of which are hereby incorporated by reference.

BACKGROUND OF THE INVENTION

Field of the Invention

The present invention relates generally to medical puncturing devices, and, more specifically, to a medical puncturing devices and methods used to take blood samples from patients.

Description of Related Art

Medical puncturing devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various medical puncturing devices are commercially available to hospitals, clinics, doctors' offices, and the like, as well as to individual consumers. Such devices typically include a sharp-pointed member such as a needle, or a sharp-edged member such as blade, that is used to make a quick puncture wound or incision in the patient's skin in order to provide a small outflow of blood. It is often physiologically and psychologically difficult for many people to prick their own finger with a hand-held needle or blade. As a result, medical puncturing devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the "automatic" force necessary to puncture or cut the skin of the patient.

It is important in the medical field that such medical puncturing devices or lancets be in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of medical puncturing device/lancet design is concerned with preventing the needle or blade of the device from wounding the user or another person after the blood sample is drawn from the patient. Once used, the needle or blade should be shielded to prevent the needle or blade from wounding the user or another person handling the device. Moreover, the medical puncturing device or lancet should be disposable to eliminate the chances of disease transmission due to the needle or blade being used on more than one person. In this regard, the medical puncturing device or lancet should ideally be designed for one firing, and have safety features to prevent reuse.

Advances have been made in recent years to increase safety in operating and handling used medical puncturing devices. For example, medical puncturing devices are currently available which are single shot devices that feature automatic ejection and retraction of the puncturing or cutting element from and into the device. Examples of such medical puncturing devices are disclosed in U.S. Pat. Nos. 6,432,120; 6,248,120; 5,755,733; and 5,540,709.

U.S. Pat. No. 6,432,120 to Teo discloses a lancet assembly that includes a lancet holder, which contains a spring-loaded lancet structure. The spring-loaded lancet structure includes a single spring that effects the ejection and retraction of a lancet needle upon the triggering of the structure. U.S. Pat. No. 6,248,120 to Wyszogrodzki discloses a puncturing device comprised of a housing, shielding portion, a piston with a puncturing tip, and drive and return springs that eject and retract the piston, respectively, upon the breakage of internal wing elements in the housing. U.S. Pat. No. 5,755,733 to Morita discloses a lancet assembly that includes a combined holder and lancet structure. The lancet structure includes a lancet member with a puncturing tip and a compressible spring member that causes the lancet member to puncture the skin of a patient upon actuation of a pair of actuating arms.

U.S. Pat. No. 5,540,709 to Ramel discloses a lancet device that includes a housing enclosing a slidable trigger, which is used to trigger a compressed spring that powers a piercing lancet member to pierce the skin of a patient. The housing includes a pair of internal fingers that engage the body of the lancet member, which are then released of engagement with the lancet member body by axial force applied by the user to the slidable trigger. Other medical puncturing devices or lancets known in the art are disclosed in U.S. Pat. Nos. 4,869,249 and 4,817,603. The devices disclosed in these references include a cap that is used to protect the needle or to keep the needle sterile.

SUMMARY OF THE INVENTION

In view of the foregoing, a need generally exists in the medical field for a medical puncturing device that ensures sterility before use and safe and secure disposal after use. Additionally, a need exists in the medical field for a simple, inexpensive, reliable, self-activating, and disposable medical puncturing device for use in collecting blood samples. Moreover, there is a need for a medical puncturing device in which production of puncture wounds and/or incisions is consistent and well-controlled.

The foregoing needs are fulfilled with a medical puncturing device in accordance with embodiments of the present invention. The medical puncturing device in one embodiment generally includes a housing, a shield, a skin puncturing assembly disposed within the housing, and preferably drive and retraction springs for axially moving the skin puncturing assembly. The housing has a proximal end and a distal end. At least one flexure member extends internally in the housing. Optionally, a pair of opposing flexure members will extend internally in the housing. The shield includes a proximal end disposed within the housing and a distal end. The shield is axially movable relative to the housing. The skin puncturing assembly includes a movable carrier and a skin puncturing element mounted to the carrier. A distal end of the skin puncturing element is adapted for puncturing the skin of a patient. The carrier is generally movable from a retracted position wherein the distal end of the skin puncturing element is disposed within the shield to a puncturing position wherein the distal end of the skin puncturing element is exposed from the shield to puncture the skin of the patient. The skin puncturing element may be a needle, for example with a sharp distal tip, or a blade with a cutting edge.

The carrier is maintained in the retracted position by engagement of the at least one flexure member with the carrier, and optionally by a pair of opposing flexure members engaged with the carrier, and moved from the retracted position to the puncturing position upon release of the at least one flexure member, or opposing flexure members, from the carrier. The drive spring is disposed within the housing, and is generally adapted to move the carrier from the retracted position to the puncturing position upon release of the at least one flexure member from the carrier. The retraction spring is disposed within the shield, and is generally adapted to return the carrier to a position within the housing wherein the shield encompasses the skin puncturing element after the carrier reaches the puncturing position.

The at least one flexure member may have a distal end engaging the carrier to maintain the carrier in the retracted position. The distal end may define a camming surface engaging an opposing camming surface on the shield proximal end, such that axial displacement of the shield into the housing causes the opposing camming surfaces to engage and release the distal end of the at least one flexure member of engagement with the carrier. More particularly, the at least one flexure member may include an inward-directed projection engaging an edge on the carrier to maintain the carrier in the retracted position. The projection may define a camming surface that engages an opposing camming surface on the shield proximal end, such that axial displacement of the shield into the housing causes the opposing camming surfaces to engage and release the projection from the carrier edge. The opposing camming surface may be oppositely tapered.

In the variation of the medical puncturing device having two opposing flexure members, distal ends of the flexure members may define tapered camming surfaces engaging an opposing, oppositely tapered camming surface on the shield proximal end. The axial displacement of the shield into the housing will cause the camming surfaces on the distal ends of the flexure members to engage the opposing, oppositely tapered camming surface on the shield proximal end and release the opposing flexure members of engagement with the carrier, permitting the drive spring to move the carrier from the retracted position to the puncturing position.

An end cap may enclose the housing proximal end. The drive spring may act between the carrier and an inner side of the end cap. The end cap may include a raised detent cooperating with a circumferential recess formed in an internal surface of the housing to connect the end cap to the housing proximal end. A removable protector cap may be provided on the shield distal end.

The shield proximal end may have at least one engagement tab adapted to engage an internal edge in the housing for limiting distal axial movement of the shield in the housing. The carrier may include at least one guide tab engaging at least one slot defined in the shield, for guiding the movement of the carrier in the shield upon release of the at least one flexure member. The at least one guide tab may be formed substantially at the carrier distal end, and the at least one slot may extend longitudinally substantially the length of the shield.

In accordance with another embodiment of the present invention, a method of actuating the medical puncturing device generally described hereinabove is provided. The method generally includes axially displacing the shield into the housing causing the distal end camming surface on the at least one flexure member to engage the opposing camming surface on the shield proximal end which releases the at least one flexure member of engagement with the carrier, such that the drive spring moves the carrier from the retracted position, wherein the distal end of the skin puncturing element is disposed within the shield, to the puncturing position, wherein the distal end is exposed from the shield to puncture the skin of the patient under the biasing force of the drive spring. Once reaching the puncturing position, the carrier is returned to a position within the housing wherein the shield encompasses the skin puncturing element under the biasing force of the retraction spring.

As indicated previously, the distal end camming surface on the at least one flexure member and the camming surface on the shield proximal end may be oppositely tapered, such that the opposing, oppositely tapered camming surfaces engage when the shield is axially displaced into the housing, which releases the at least one flexure member of engagement with the carrier. The engagement of the opposing, oppositely tapered camming surfaces causes the at least one flexure member to flex radially out of engagement with the carrier.

The method may further include removing the protector cap from the shield distal end prior to axially displacing the shield into the housing. The at least one guide tab on the carrier may engage the at least one slot defined in the shield, such that movement of the carrier from the retracted position to the puncturing position is guided by the at least one guided tab received in the at least one slot.

In another embodiment, the medical puncturing device includes a housing, a shield, and a skin puncturing assembly disposed within the housing. The housing has a proximal end and a distal end. The shield has a proximal end and a distal end. The shield proximal end is disposed within the housing. The shield is axially movable relative to the housing. The skin puncturing assembly generally includes a movable carrier and a skin puncturing element mounted to the carrier. The skin puncturing element includes a distal tip end adapted to puncture the skin of a patient. The skin puncturing element may be a needle, for example with a sharp distal tip, or a blade with a cutting edge.

The carrier is generally movable from a retracted position wherein the distal end of the skin puncturing element is disposed within the shield to a puncturing position wherein the distal end is exposed from the shield to puncture the skin of the patient. The carrier is maintained in the retracted position by engagement of at least one retaining tab on the shield with the carrier, and moved from the retracted position to the puncturing position upon release of the retaining tab.

A drive spring may be disposed within the housing and be adapted to move the carrier from the retracted position to the puncturing position upon release of the at least one retaining tab from the carrier. A retraction spring may be disposed within the shield and be adapted to return the carrier to a position within the housing wherein the shield encompasses the skin puncturing element after the carrier reaches the puncturing position.

The at least one retaining tab may be disposed internally in the shield and engage at least one guide tab on the carrier to maintain the carrier in the retracted position. The medical puncturing device according to this embodiment may further include an actuating member extending internally in the housing. The actuating member may define a distal end camming surface engaging an opposing camming surface on the shield proximal end, such that axial displacement of the shield into the housing causes the opposing camming surfaces to engage and release the at least one retaining tab of engagement with the at least one guide tab. The camming surface on the actuating member distal end and the camming surface on the shield proximal end may be oppositely tapered.

In accordance with another embodiment of the present invention, a method is provided for actuating the medical puncturing device described hereinabove. The method includes axially displacing the shield into the housing, which causes the distal end camming surface on the actuating member to engage the camming surface on the shield proximal end and release the at least one retaining tab of engagement with a carrier, such that the drive spring moves the carrier from the retracted position, wherein the distal end of the skin puncturing element is disposed within the shield, to the puncturing position, wherein the distal end is exposed from the shield to puncture the skin of the patient under the biasing force of the drive spring. The retraction spring may be used to return the carrier to a position within the housing, wherein the shield encompasses the skin puncturing element. The engagement of the opposing camming surfaces generally causes the shield proximal end to deform radially and release the at least one retaining tab of engagement with the at least one guide tab.

As indicated previously, the at least one retaining tab may be disposed internally in the shield and cooperate with the at least one guide tab on the carrier to maintain the carrier in a retracted position until the shield is axially displaced into the housing. The distal end camming surface on the actuating member and the opposing camming surface on the shield proximal end may be oppositely tapered, such that the opposing, oppositely tapered camming surfaces engage when the shield is axially displaced into the housing and release the at least one retaining tab of engagement with the at least one guide tab. The engagement of the opposing, oppositely tapered camming surfaces may cause the shield proximal end to deform radially and release the at least one retaining tab of engagement with the at least one guide tab.

Further details and advantages of the present invention will become apparent from the following detailed description when read in conjunction with the accompanying drawings.

BRIEF DESCRIPTION OF THE DRAWINGS

FIG. 3 is a perspective view of a housing portion of the medical puncturing device of FIG. 1, showing hidden lines;

FIG. 4 is a perspective view of a shield portion of the medical puncturing device of FIG. 1, showing hidden lines;

FIG. 5 is a perspective view of an end cap portion of the medical puncturing device of FIG. 1;

DETAILED DESCRIPTION OF THE INVENTION

Figure 1:
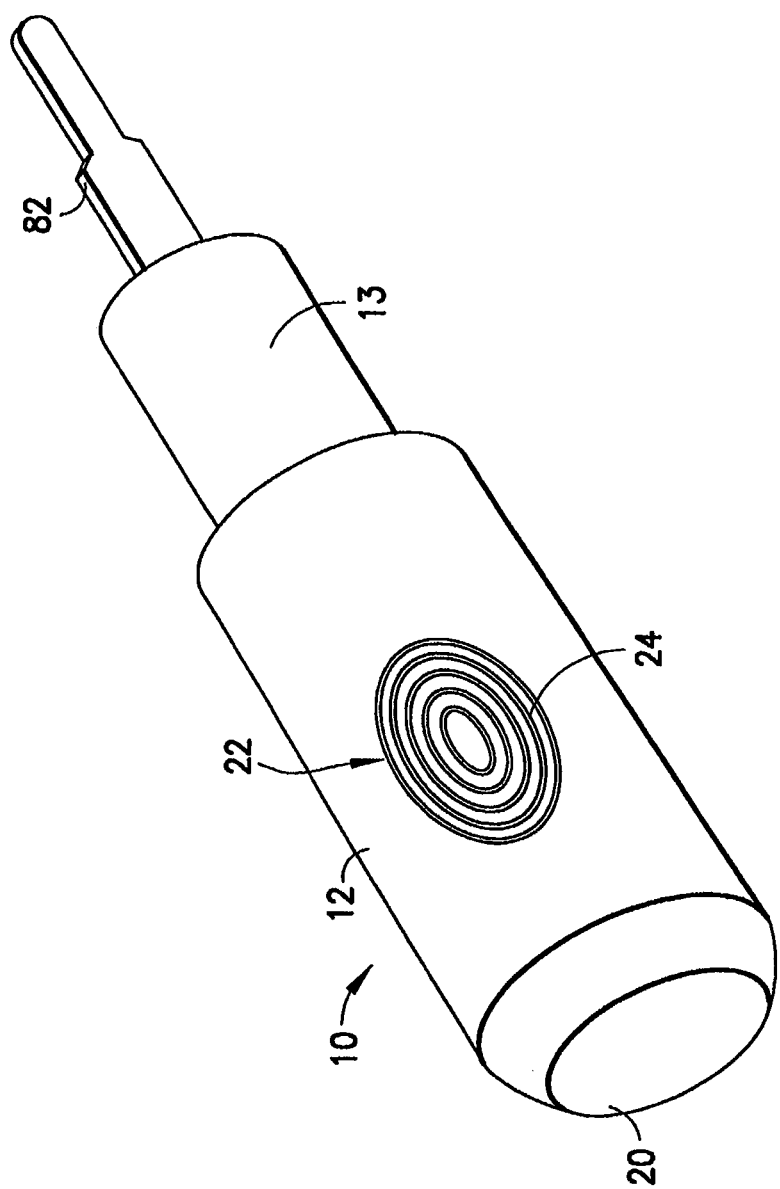
FIG. 1 is a perspective view of a medical puncturing device in accordance with an embodiment of the present invention, showing the device with a removable tip guard.

For purposes of the description hereinafter, the terms "upper", "lower", "right", "left", "vertical", "horizontal", "top", "bottom", and derivatives thereof shall relate to the embodiments of the invention, as it is oriented in the drawing figures. However, it is to be understood that the embodiments may assume many alternative variations and step sequences except where expressly specified to the contrary. It is also to be understood that the specific devices and processes illustrated in the attached drawings and described in the following text are simply exemplary embodiments of the invention. Hence, specific dimensions and other physical characteristics related to the embodiments disclosed hereinafter are not to be considered limiting.

Referring to FIGS. 1-5, a medical puncturing device or lancet 10 (hereinafter "puncturing device 10") in accordance with a first embodiment of the present invention is generally illustrated. The puncturing device 10 generally includes a housing 12, a shield 13 received partially within and axially movable relative to the housing 12, and a skin puncturing assembly 14 disposed within the housing 12. The housing 12 is preferably a generally tubular structure having a distal end 16 and a proximal end 18. The housing 12 may be open-ended at the distal and proximal ends 16, 18. An end cap 20 may be provided at the proximal end 16 of the housing 12 to close the proximal end 18 of the housing 12. Alternatively, the housing 12 may be formed to have a closed proximal end 18 instead of the end cap 20. The closed proximal end 18 of the housing 12 would be integrally formed with the remainder of the body of the housing 12 in this variation of the puncturing device 10.

Preferably, the housing 12 is made of a substantially rigid material such as a hard plastic, preferably a medical grade plastic. The end cap 20 may also be made of a similar material to the housing 12. The housing 12 may have any suitable cross-sectional shape, such as oval, circular, or polygonal. However, because the housing 12 is intended to be grasped between the fingertips of the user of the puncturing device 10, the cross-sectional shape of the housing 12 is preferably selected so that the housing 12 is easily manipulated by the user's fingertips. An oval or circular cross-sectional shape for the housing 12 best fits this requirement and is presently preferred, as depicted in FIG. 3.

Additionally, the housing 12 is preferably formed with finger pads 22 provided on opposing sides of the housing 12 for grasping by the user of the puncturing device 10. One of the finger pads 22 as illustrated in FIG. 1, and is formed by concentric oval rings 24 that are raised from an outer or external surface 26 of the housing 12. The fingerpads 22 provide gripping surfaces for the user of the puncturing device 10, and also provide a tactile indication of where the user of the puncturing device 10 should place his or her fingertips when actuating the puncturing device 10 in the manner described herein. The shield 13 preferably has a cross-sectional shape that corresponds to the housing 12, and may be circular, oval, or polygonal in transverse cross-section in a similar manner to the housing 12. A preferred circular cross-sectional shape for the shield 13 is depicted in FIG. 4.

The housing 12 has a generally uniform wall thickness over its length up to a distal portion 28 of the housing 12, where the wall thickness of the housing increases. The increased wall thickness of the distal portion 28 of the housing 12 forms an internal edge 30, preferably a circumferentially-extending internal edge 30, within the housing 12 that limits the axial distal movement of the shield 13 relative to the housing 12 as discussed herein. The increased wall thickness distal portion 28 of the housing 12 extends or forms approximately 10-40% of the length of the housing 12 and generally forms the distal end 16 of the housing 12.

The end cap 20, if present, is engaged with the housing 12 by a frictional, snap-fit type of engagement. Once engaged with the housing 12, the frictional engagement between the end cap 20 and housing 12 is preferably of sufficient strength to prevent the end cap 20 from being removed easily from the housing 12 to reduce the ability of a user of the puncturing device 10 to tamper with the puncturing device 10 after manufacturing. In particular, the end cap 20 includes a circumferential detent 32 that cooperates with a circumferential recess 34 formed in an internal or interior surface 36 of the housing 12. To further secure the connection between the end cap 20 and housing 12, a medical-type adhesive may be provided in the recess 34 during the assembling process for the puncturing device 10, thereby adhesively securing the detent 32 in the recess 34. The end cap 20 further includes at least one and preferably a pair (i.e., a plurality) of opposing flexure members 38 extending internally into the housing 12 from an inner side 40 of the end cap 12. The flexure members 38 may be integrally formed with the end cap 20, as illustrated in FIG. 2.

The shield 13 includes a distal end 42 and a proximal end 44. The shield 13 is disposed partially in the housing 12, and is axially movable relative to the housing 12. The proximal end 44 of the shield 13 is disposed within the housing 12. As shown in FIG. 2, the distal end 42 of the shield 13 is preferably formed with an internally-extending portion 46. The internally-extending portion 46 defines a recess or pocket 48 for housing a spring or other biasing element, as discussed further herein.

The shield 13 further includes at least one and preferably a plurality of projections or engagement tabs 49 provided or formed at the proximal end 44 of the shield 13. The projections or engagement tabs 49 generally cooperate or engage with the internal surface 36 of the housing 12. The engagement tabs 49 are generally further adapted to engage or contact the internal edge 30 formed by the distal portion 28 of the housing 12. The interference engagement of the engagement tabs 49 with the internal edge 30 limits the ultimate axial distal movement of the shield 13 relative to the housing 12, and further prevents the shield 13 from being removed from the distal end 16 of the housing 12 once inserted therein during manufacturing. The interference engagement of the engagement tabs 49 with the internal edge 30 thus minimizes the ability of a user of the puncturing device 10 to tamper with the puncturing device 10 after manufacturing. The engagement tabs 49 may also be used to guide the movement of the shield 13 proximally into the housing 12, and thereby function as internal guiding elements for the shield 13. For example, the engagement tabs 49 may be configured to engage internal guide tracks/or grooves (not shown) formed internally in the housing 12. Such internal guide tracks/or grooves, if provided, may extend from an area proximate to the end cap 20 to the distal portion 28 of the housing 12.

Figure 2:
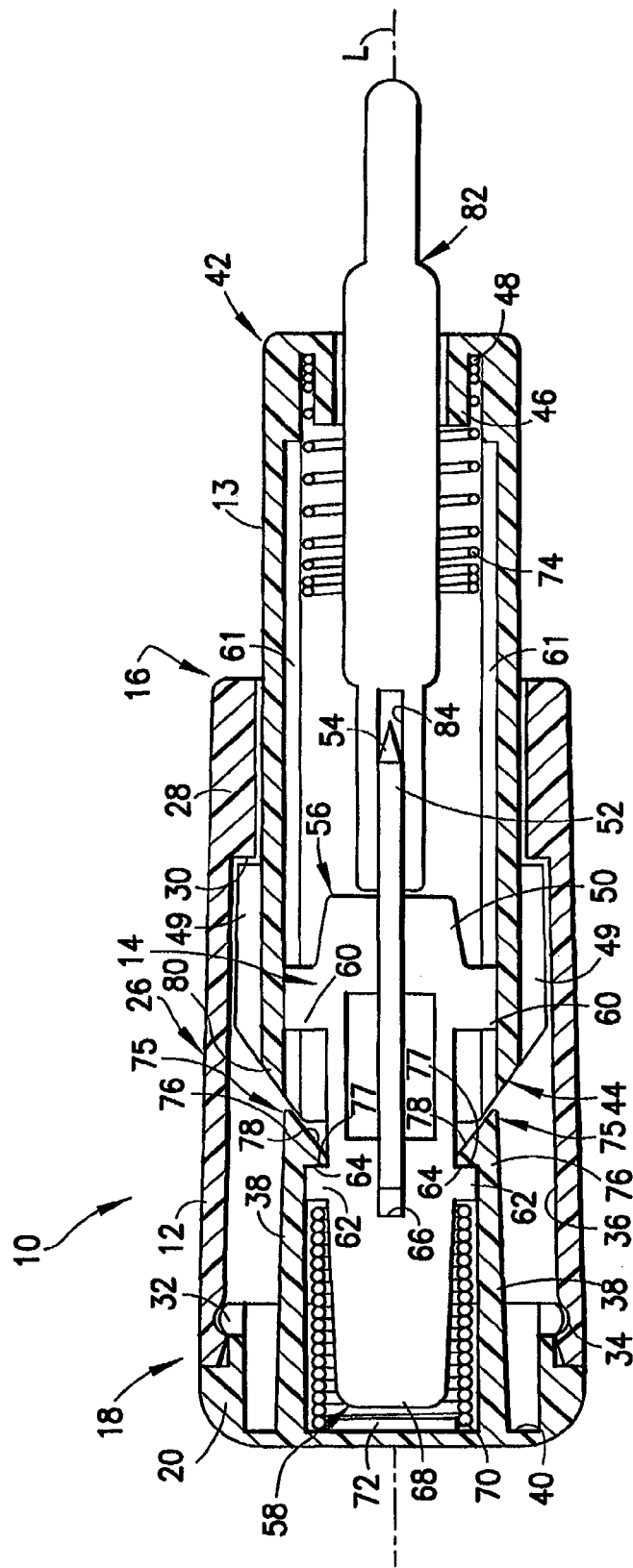
FIG. 2 is a longitudinal cross-sectional view of the medical puncturing device of FIG. 1.

As shown in FIG. 2, the skin puncturing assembly 14 is generally disposed within the housing 12 proximally of the distal portion 28 of the housing 12 and partially within the shield 13. The skin puncturing assembly 14 is axially movable relative to the housing 12 and shield 13. The skin puncturing assembly 14 generally includes an elongated carrier member 50 (hereinafter "carrier 50") and a skin puncturing element 52. The skin puncturing element 52 may be a needle, blade, or like puncturing or cutting element, and includes a sharp distal tip 54 for puncturing or cutting the skin of a patient from which a blood sample is to be taken. The carrier 50 preferably has a generally cylindrical shape to fit within the preferred circular or oval cross-sectional shape of the housing 12 and shield 13. However, other cross-sectional shapes for the carrier 50, such as polygonal, may be used in alternative embodiments of the present invention.

The carrier 50 includes a first or distal end 56 and a second or proximal end 58. The distal end 56 is generally received in the shield 13 prior to actuation of the puncturing device 10. The proximal end 58 of the carrier 50 extends toward the proximal end 18 of the housing and is generally engaged by the flexure members 38 extending from the end cap 20. The engagement of the flexure members 38 with the carrier 50 maintains the positioning of the carrier 50 in the housing 12 and shield 13 prior to actuation of the puncturing device 10, as discussed further herein. The body of the carrier 50 is preferably formed with at least one and preferably two or more distal guide tabs 60. The guide tabs 60 are adapted to cooperate with respective longitudinal slots or grooves 61 formed or defined in the body of the shield 13. The slots or grooves 61 are formed or defined internally in the shield 13, and guide the axial distal movement of the carrier 50 relative to the shield 13 when the puncturing device 10 is actuated, as discussed further herein.

The body of the carrier 50 is also formed with a circumferentially-extending proximal protrusion or projection 62. The proximal protrusion 62 forms a circumferential edge 64 on the body of the carrier 50 that is engaged by the flexure members 38 to maintain the positioning of the carrier 50 in the housing 12 and shield 13 prior to actuation of the puncturing device 10. The proximal protrusion 62 preferably has a diameter no larger than the diameter of the guide tabs 60 to enable movement of the proximal end 58 of the carrier 50 into the shield 13 during actuation of the puncturing device 10, as discussed further herein. The proximal protrusion 62 need not extend entirely around the circumference of the carrier 50, and may be provided as two individual protrusions or projections located on opposite sides of the carrier 50 for engagement by the flexure members 38 to maintain the positioning of the carrier 50 in the housing 12 and shield 13.

The skin puncturing element 52 generally extends from the distal end 56 of the carrier 50 and is received within a central bore 66 formed centrally within the body of the carrier 50. The skin puncturing element 52 may be secured in the central bore 66 by a medical grade adhesive or by other means customary in the medical field. The skin puncturing element 52 is depicted in the Figures of this disclosure as a needle. However, as indicated previously, the skin puncturing element 52 is not necessarily limited to a needle or other puncturing-type element, but could also be a blade for causing an incision-type wound in the skin of a patient when the puncturing device 10 is activated.

Preferably, the carrier 50 further includes a cylindrical-shaped proximal portion 68 at the proximal end 58 of the carrier 50. The proximal portion 68 preferably extends from the proximal protrusion 62 toward the inner side 40 of the end cap 20. Preferably, the proximal portion 68 tapers inward toward a central axis L of the puncturing device 10, such that the proximal portion 68 reduces in diameter toward the proximal end 58 of the carrier 50.

Figure 8:
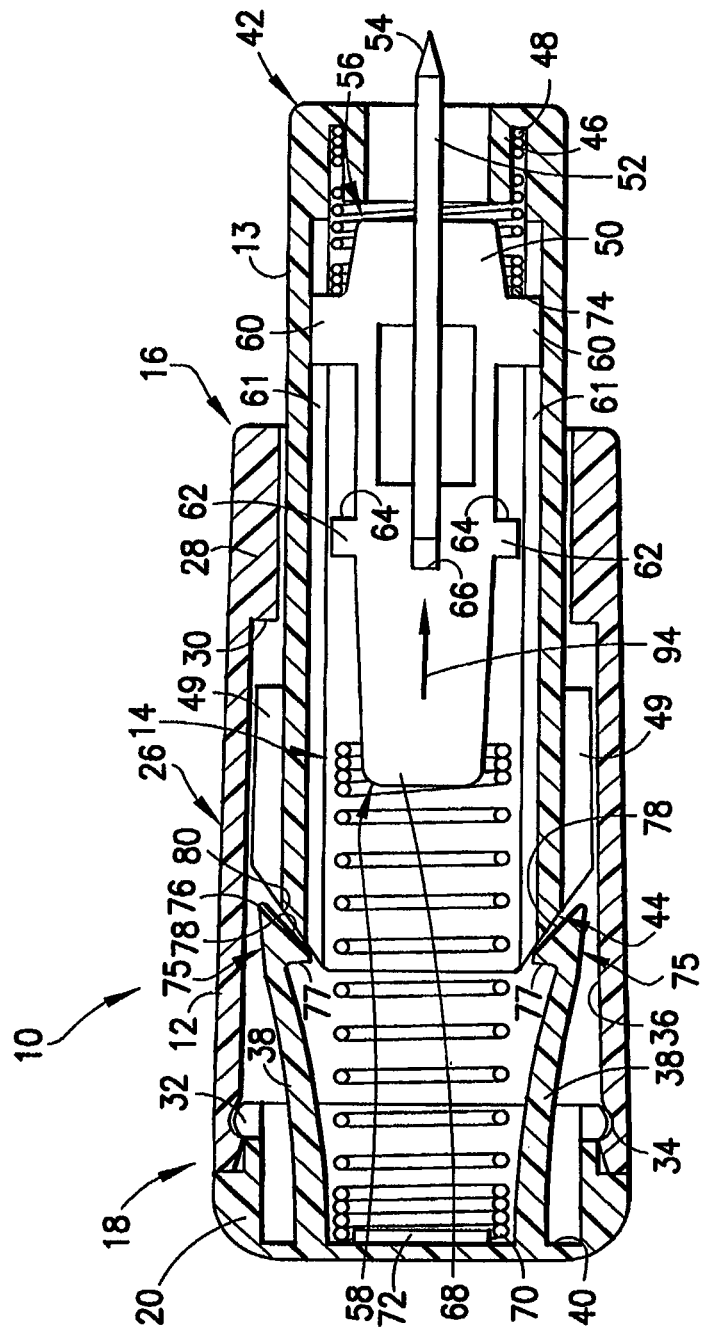
FIG. 8 is a longitudinal cross-sectional view of the medical puncturing device of FIG. 1, showing the device immediately after actuation with a skin piercing element of the device exposed momentarily for piercing the skin of a patient.

The puncturing device 10 further includes a drive or firing spring 70 disposed in the housing 12 and received at least partially about the carrier 50. The drive spring 70, when actuated or released, provides the force necessary to move the skin puncturing assembly 14 distally within the housing 12 and through the shield 13. The drive spring 70 further provides the force necessary to puncture the skin of a patient when the puncturing device 10 is used in a blood-drawing or collecting procedure. More particularly, the drive spring 70 is adapted to move the carrier 50 within the housing 12 from the retracted position shown in FIG. 2 to an extended or puncturing position as shown in FIG. 8 discussed herein. In the retracted position of the carrier 50, the sharp distal tip 54 of the skin puncturing element 52 is contained in the housing 12 and, more particularly, the shield 13. In the extended or puncturing position, the skin puncturing element 52 extends outward from the distal end 16 of the shield 13, and the sharp distal tip 54 of the skin puncturing element 52 is exposed for causing a puncturing or incision-type wound in the skin of a patient.

The drive spring 70 is generally received about the tapered proximal portion 68 of the carrier 50. The tapering of the proximal portion 68 ensures that there is a tight frictional engagement between the drive spring 70 and the carrier 50. However, the proximal portion 68 may be formed to have a substantially uniform diameter along its length, and the drive spring 70 may be secured to the proximal portion 68 by other means customary in the medical field, such as with a medical adhesive or by a simple mechanical fastener or like element. The drive spring 70 generally extends between the proximal portion 68 of the carrier 50 and the inner side 40 of the end cap 20. The inner side 40 of the end cap 20 may include a centering protrusion or projection 72 adapted to maintain the positioning of the drive spring 70 prior to and during actuation of the puncturing device 10. As shown in FIG. 2, the drive spring 70 is held in a compressed state within the housing 12 prior to actuation of the puncturing device 10 by the engagement of the flexure members 38 with the circumferential edge 64 formed by the proximal protrusion 62 on the carrier 50. The drive spring 70 is generally compressed between the tapered proximal portion 68 and the inner side 40 of the end cap 20 and, optionally, between the proximal protrusion 62 on the carrier 50 and the inner side 40 of the end cap 20.

The puncturing device 10 further includes a return or retraction spring 74 disposed in the shield 13 to provide the force necessary to generally return the skin puncturing assembly 14 to a static condition within the housing 12 and shield 13 after the puncturing device 10 is actuated by a user. More particularly, the retraction spring 74 provides the force necessary to return the carrier 50 to a position within the housing 12 and shield 13 wherein the skin puncturing element 52 and sharp distal tip 54 thereof are fully contained within the housing 12 and shield 13. As indicated previously, during actuation of the puncturing device 10, the drive spring 70 generally moves the carrier 50 from the retracted position shown in FIG. 2, to an exposed or puncturing position (shown in FIG. 8 discussed herein), wherein the sharp distal tip 54 of the skin puncturing element 52 extends from the distal end 42 of the shield 13 for causing a puncturing or incision-type wound in the skin of a patient. The retraction spring 74 is used to return the carrier 50 to a position within the housing 12 and shield 13 wherein the skin puncturing element 52 and the sharp distal tip 54 thereof is fully contained within the housing 12 and shield 13.

The retraction spring 74 is generally seated in the pocket 48 formed by the internally-extending portion 46 of the shield 13. The retraction spring 74 generally acts on the distal end 56 of the carrier 50 as the drive spring 70 biases the carrier 50 toward the distal end 16 of the housing 12 and, further, the distal end 42 of the shield 13 when the puncturing device 10 is actuated by a user. The retraction spring 74 is in a generally uncompressed state prior to actuation of the puncturing device 10 as shown in FIG. 2. The retraction spring 74 may be secured in the pocket 48 formed by the internally-extending portion 46 of the shield 13 by a suitable medical grade adhesive, if desired. Otherwise, a simple frictional engagement between the retraction spring 74 and the pocket 48 secures the retraction spring 74 to the shield 13 in accordance with an embodiment of the present invention.

As indicated previously, the engagement of the flexure members 38 with the circumferential edge 64 formed by the proximal protrusion 62 on the carrier 50 maintains the drive spring 70 in a compressed, pre-actuated state or condition. In particular, distal ends 75 of the flexure members 38 engage the proximal protrusion 62 on the carrier 50 to maintain the drive spring 70 in the compressed, pre-actuated state. The distal end 75 of the flexure members 38 preferably include inward-directed projections 76, which engage the circumferential edge 64 formed by the proximal protrusion 62 on the carrier 50 to maintain the drive spring 70 in the compressed, pre-actuated state. The projections 76 define engagement edges 77 that engage the circumferential edge 64 formed by the proximal protrusion 62 on the carrier 50 to maintain the drive spring 70 in the compressed, pre-actuated state. Additionally, the projections 76 preferably further define respective camming surfaces 78. The camming surfaces 78 are preferably tapered inward toward the central axis L of the puncturing device 10.

As shown in FIG. 2, the distal ends 75 of the flexure members 38 are generally in contact or engagement with the proximal end 44 of the shield 13. The proximal end 44 of the shield 13 preferably defines a tapered camming surface 80, which engages or cooperates with the camming surfaces 78 formed at the distal ends 75 of the flexure members 38. The camming surface 80 is preferably oppositely tapered from the camming surfaces 78. Thus, the camming surface 80 preferably tapers away from the central axis L of the puncturing device 10.

The skin puncturing assembly 14 may further include a protective tip guard 82 connected to the carrier 50. The tip guard 82 may be formed integrally with the body of the carrier 50, but include a notched connection with the distal end 56 of the carrier 50. Alternatively, as shown in FIG. 2, the tip guard 82 may define a central bore 84, which receives the skin puncturing element 82 and, further, the sharp distal tip 54 thereof. The tip guard 82 preferably extends outward from the distal end 16 of the housing 12 and distal end 42 of the shield 13 shown in FIGS. 1 and 2. If a notched connection is provided between the tip guard 82 and the carrier 50, this connection enables the user of the puncturing device 10 to break the integral connection between the tip guard 82 and carrier 50, and remove the tip guard 82 prior to actuating the puncturing device 10. The tip guard 82 ensures that the sharp distal tip 54 of the puncturing element 52 remains sterile before use and, further, protects the user against accidental puncture wounds that could be caused by inadvertent or premature actuation of the puncturing device 10. The tip guard 82 may be removed by simply pulling on the tip guard 82 and/or moving the tip guard 82 in a side-to-side manner in the open distal end 16 of the housing 12 until the notched connection with the carrier 50 breaks, as is well-known in the art.

The assembly of the puncturing device 10 is a simple and straight forward process. The housing 12 is typically provided first and, as discussed previously, includes the open distal and proximal ends 16, 18. Next, the shield 13 preferably containing the retraction spring 74 may be inserted into the open proximal end 18 of the housing 12, such that the distal end 42 of the shield 13 extends from the distal end 16 of the housing 12. The engagement of the engagement tabs 49 with the internal edge 30 defined by the distal portion 28 of the housing 12 limits the distal movement of the shield 13 relative to the housing 12. Once the shield 13 is in place, the skin puncturing assembly 14 may be inserted into the open proximal end 18 of the housing 12. The skin puncturing assembly 14 is generally inserted into the housing 12 so that the distal guide tabs 60 slidably cooperate with the longitudinal slots 61 formed in the shield 13.

With the skin puncturing assembly 14 in place within the housing 12 and shield 13, the drive spring 70 may be inserted into the housing 12 through the open proximal end 18 of the housing 12. The drive spring 70 is received about the tapered proximal portion 68 of the carrier 50 and extends from the tapered proximal portion 68 towards the open proximal end 18 of the housing 12. The housing proximal end 18 is then closed with the end cap 20. The drive spring 70 is generally placed in a compressed, pre-actuated state within the housing 12 by affixing the end cap 20 to the housing proximal end 18. In particular, the flexure members 38 are placed in engagement with the proximal protrusion 62 on the carrier 50 which compresses the drive spring 70 about the carrier 50. The end cap 20 is secured to the housing 12 by engagement of the detent 32 on the end cap 20 with the recess 34 in the housing 12. The assembled puncturing device 10 is now ready for use.

Figure 6:
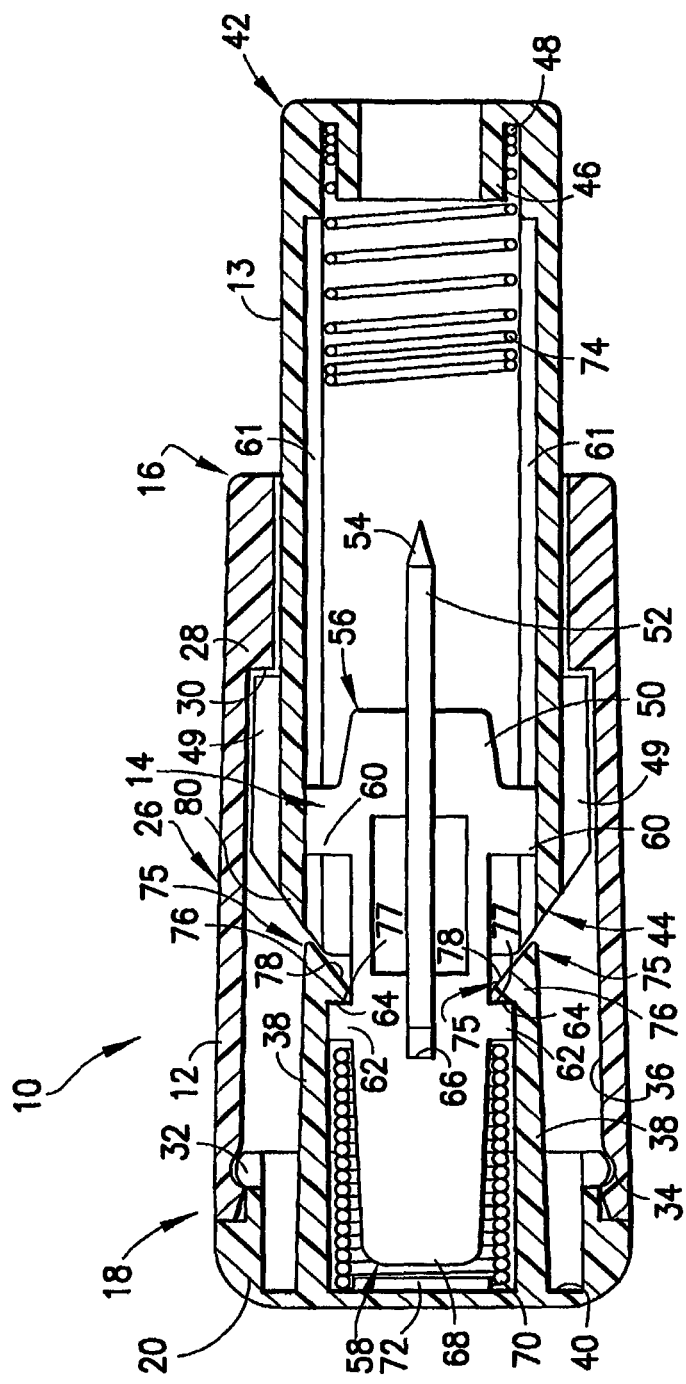
FIG. 6 is a longitudinal cross-sectional view of the medical puncturing device of FIG. 1, showing the device prior to actuation and with the tip guard removed.
Figure 7:
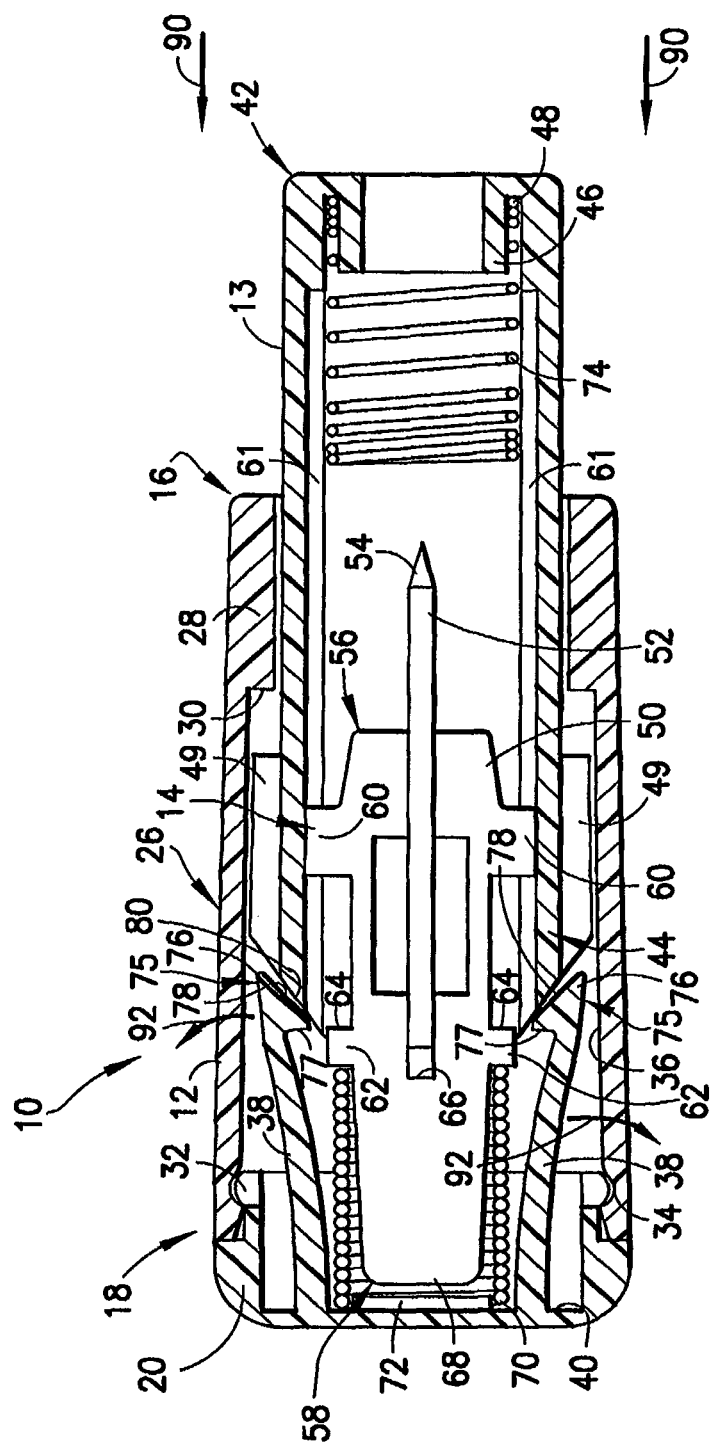
FIG. 7 is a longitudinal cross-sectional view of the medical puncturing device of FIG. 1, showing the device during actuation and the direction of forces applied to actuate the device.

Referring to FIGS. 6-9, the sequence of actuation for the puncturing device 10 will now be discussed. FIG. 6 shows the puncturing device 10 in a pre-actuated state in a similar manner to FIG. 4 discussed previously but with the tip guard 82 removed. In the pre-actuated state, the flexure members 38 are in engagement with the carrier 50. The engagement of the flexure members 38 with the carrier 50 maintains the drive spring 70 in a compressed state between the end cap 20 and the proximal portion 68 of the carrier and, optionally, between the end cap 20 and the proximal protrusion 62. Additionally, in the pre-actuated state, the retraction spring 74 is disposed in the pocket 24 formed at the distal end 42 of the shield 13 and is in an uncompressed or untensioned state.

To actuate the puncturing device 10, the user grasps the housing 12 between the thumb and forefinger, preferably with the thumb and forefinger substantially engaging the fingerpads 22 on the external surface 26 of the housing 12. The user then places the distal end 42 of the shield 13 in contact with the body part where a blood sample is to be taken. The user exerts a distally-directed force on the housing 12, which causes the shield 13 to move proximally into the housing 12 in the direction of arrows 90 in FIG. 6. This simultaneously causes the proximal end 44 of the shield 13 to contact or engage the flexure members 38. In particular, the camming surface 80 on the proximal end 44 of the shield 13 engages the camming surfaces 78 on the inward-directed projections 76 of the flexure members 38, which causes the flexure members 38 to move or spread radially apart, as represented by arrows 92 in FIG. 7. Once the interference engagement between the flexure members 38 and the proximal protrusion 62 on the carrier 50 is released, the compressed drive spring 70 is also released. The drive spring 70 automatically biases or drives the carrier 50 toward the distal end 16 of the housing 12 and distal end 42 of the shield 13. The engagement of the distal guide tabs 60 on the carrier 50 with the longitudinal slots 61 in the shield 13 guides the movement of the carrier 50 in the housing 12 and in the shield 13.

FIG. 8 shows the released movement of the carrier 50 in the housing 12 and shield 13. The carrier 50 is released from the retracted position or configuration shown in FIG. 6 and moves to a puncturing position or configuration shown in FIG. 8, wherein the puncturing element 52 extends from the distal end 42 of the shield 13 and the sharp distal tip 54 of the puncturing element 52 is fully exposed for piercing or cutting the skin of a patient. The direction of movement of the carrier 50 in the housing 12 and shield 13 upon actuation of the puncturing device 10 is identified by arrow 94 in FIG. 8. In the puncturing position or configuration shown in FIG. 8, the skin puncturing element 52 of the skin puncturing assembly 14 reaches its maximum extension from the distal end 42 of the shield 13 and is driven under the force of the drive spring 70 into the skin of the patient (not shown). The drive spring 70 preferably has sufficient stored energy to cause the sharp distal tip 54 of the skin puncturing element 52 to pierce the skin of a person or animal once the flexure members 38 are released of engagement with the carrier 50.

Figure 9:
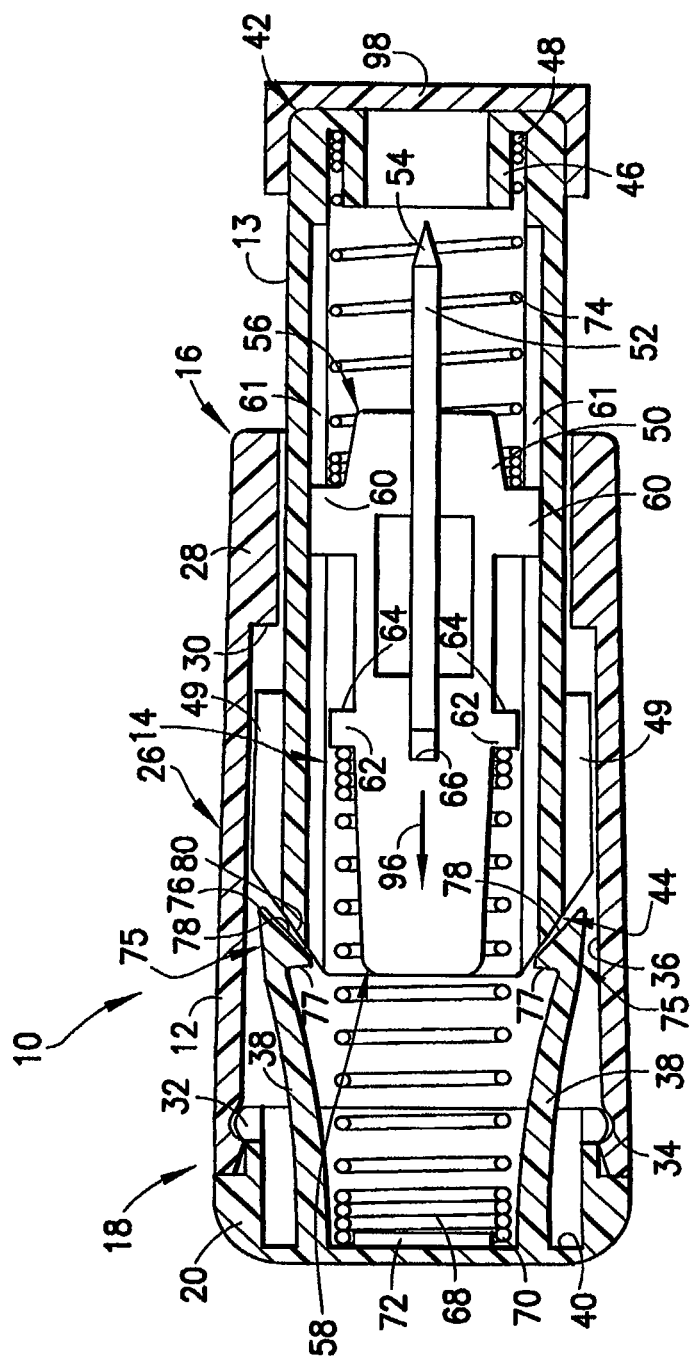
FIG. 9 is a longitudinal cross-sectional view of the medical puncturing device of FIG. 1, showing the device after actuation with the skin piercing element returned to a position in the shield portion.

FIG. 9 shows the ultimate disposition of the carrier 50 within the housing 12 and shield 13 after the puncturing device 10 has been actuated. As shown in FIG. 8, as the carrier 50 reaches the puncturing position wherein the sharp distal tip 54 of the skin puncturing element 52 is fully exposed, the retraction spring 74 is compressed between the distal guide tabs 60 on the carrier 50 and the distal end 42 of the shield 13. The retraction spring 74 is compressed in the pocket 48. The compression of the retraction spring 74 provides a return or retraction force that acts on the carrier 50 to move the carrier 50 in a return or retraction direction in the housing 12 as identified with arrow 96 in FIG. 9, which returns or retracts the skin puncturing element 52 and the sharp distal tip 54 thereof fully into the housing 12 and shield 13. The retraction spring 74 thereafter prevents the reemergence of the skin puncturing element 52 from the housing 12 and shield 13. If desired, a protector cap 98 may be provided to enclose the distal end 42 of the shield 13 to further ensure that the skin puncturing element 52 will not extend outward from the shield 13 after the puncturing device 10 has been activated. The protector cap 98 is removable from the shield 13 and may generally take the place of the tip guard 82 discussed previously. Thus, the removable protector cap 98 may be provided on the distal end 42 of the shield 13 prior to actuation of the puncturing device 10 and reapplied or replaced thereon after the puncturing device 10 has been actuated.

Figure 10:
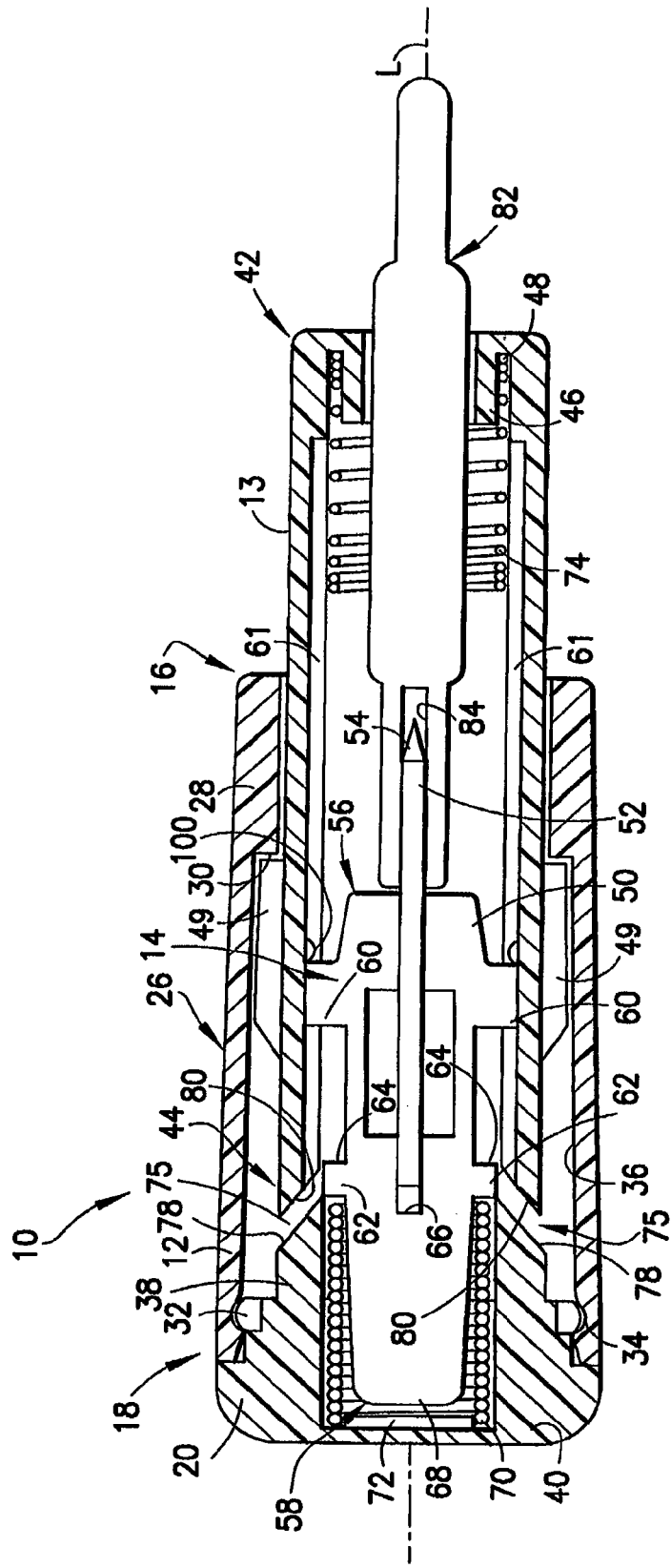
FIG. 10 is a longitudinal cross-sectional view of an alternative embodiment of the medical puncturing device in accordance with an embodiment of the present invention.
Figure 12:
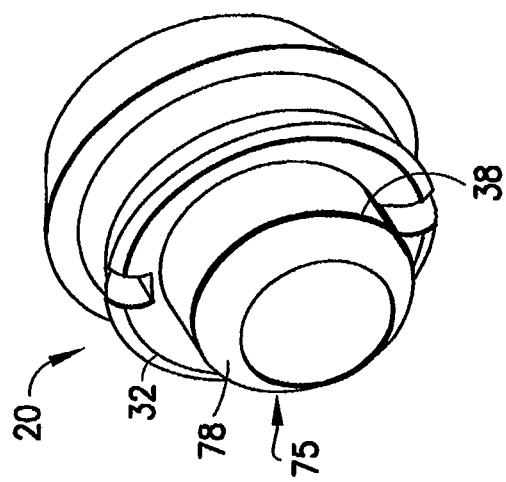
FIG. 12 is a perspective view of an end cap used in the alternative embodiment of the device shown in FIG. 10.
Figure 11:
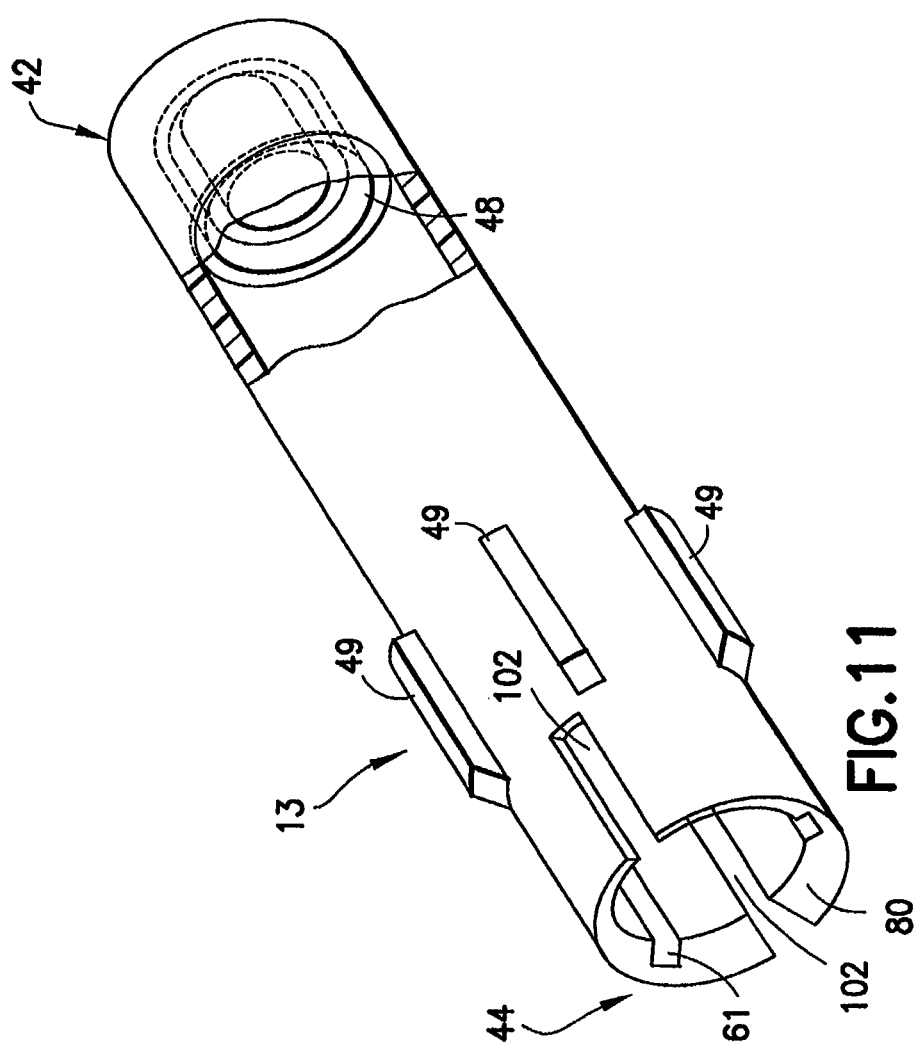
FIG. 11 is a perspective view of a shield portion used in the alternative embodiment of the device shown in FIG. 10.

Referring to FIGS. 10-12, another embodiment of the puncturing device 10 is shown. In the puncturing device 10, the carrier member 50 is no longer maintained in the retracted position by the flexure members 38. In the puncturing device 10 illustrated in FIGS. 10-12, one or more retaining tabs 100 is provided internally in the shield 13. The retaining tabs 100 maintain the positioning of the carrier 50 in the shield 13, and, further, compression of the drive spring 70 until actuation of the puncturing device 10. The flexure members 38 previously provided on the end cap 40 are now replaced or formed as a singular actuating member 101 extending from the end cap 40.

The puncturing device 10 shown in FIGS. 10-12 is actuated in a slightly different manner than the puncturing device 10 illustrated in FIGS. 1-9. The proximal end 44 of the shield is now adapted to be radially deformed or flexed outward by the distal ends 75 of preferably the singular actuating member 101 when the shield 13 is axially displaced into the housing 12. To provide for this outward radial displacement, the proximal end 44 of the shield 13 defines at least one and, preferably, at least two opposing slots 102, 104. The proximal end 44 of the shield 13 also extends further into the housing 12, as shown in FIG. 10. The camming surface 80 on the proximal end 44 of the shield 13 is also tapered in an opposite direction from the configuration used in the puncturing device 10 discussed previously in connection with FIGS. 1-9.

In the puncturing device 10 illustrated in FIGS. 10-12 the distal end 44 of the actuating member 101 defines a camming surface 78 that is oppositely tapered from the camming surfaces 78 on the distal ends 75 of the flexure members 38 discussed previously in connection with FIGS. 1-9. The actuating member 101 is now adapted to engage the proximal end 44 of the shield 13 and radially deform or flex the proximal end 44 of the shield 13 to permit the drive spring 70 to move the carrier 50 within the housing 12 and shield 13. In particular, the camming surface 78 on the distal end 75 of the actuating member 101 engages the oppositely tapered and opposing camming surface 80 on the proximal end 44 of the shield 13, such that the proximal end 44 of the shield 13 deforms or flexes radially outward by virtue of the slots 102, 104 when the shield is displaced into the housing 12. The opposing camming surfaces 78, 80 are preferably configured to deform the proximal end 44 of the shield 13 sufficiently radially outward, which is facilitated by the opposing slots 102, 104, to release the retaining tabs 100 from engagement with the carrier 50. In particular, the retaining tabs 100 are released of engagement with the guide tabs 60 formed on the carrier 50 proximate to the distal end 56 of the carrier 50. Once the retaining tabs 100 are released of engagement, the carrier 50 will be displaced by the drive spring 70 in the manner discussed previously in connection with the puncturing device 10 illustrated in FIGS. 2-9. Other than the specific changes discussed hereinabove, the puncturing device 10 shown in FIGS. 10-12 is identical in all other respects to the puncturing device 10 discussed previously in connection with FIGS. 2-9.

While the present invention was described with reference to preferred embodiments of the medical puncturing device, those skilled in the art may make modifications and alterations to the present invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

What is claimed is:

1. A lancet device, comprising:
a housing having a proximal end and a distal end;
a shield having a proximal end and a distal end, the shield proximal end disposed within the housing, and the shield being movable relative to the housing;
a skin puncturing assembly disposed within the housing and comprising a movable carrier and a skin puncturing element, a distal end of the skin puncturing element adapted for puncturing the skin of a patient, the carrier movable between a first position where the distal end of the skin puncturing element is disposed within the shield, and a second position where the distal end extends out of the shield in a puncturing position;
at least one flexure member transitionable between a first state in which the at least one flexure member engages the carrier to maintain the carrier in the first position, and a second state in which the at least one flexure member does not engage the carrier and the carrier is movable from the first position to the second position;
a drive spring disposed within the housing and in contact with a portion of the carrier for biasing the carrier from the first position to the second position when the at least one flexure member is in the second state, wherein the drive spring biases the carrier toward the distal end of the shield; and
a retraction spring disposed within the shield, the retraction spring adapted to return the carrier to a position within the housing wherein the shield encompasses the skin puncturing element after the carrier reaches the puncturing position,
wherein the at least one flexure member is transitioned from the first state to the second state by a portion of the proximal end of the shield contacting a portion of the at least one flexure member thereby moving the at least one flexure member radially outward.

2. The lancet device of claim 1, wherein the shield is axially movable into the housing, and wherein the at least one flexure member is caused to change from the first state to the second state by contact with a surface as the shield is caused to move into the housing.

3. The lancet device of claim 1, wherein the at least one flexure member is generally annular.

4. The lancet device of claim 1, wherein the at least one flexure member further comprises a surface that engages a surface of the carrier to maintain the carrier in the first position.

5. The lancet device of claim 4, wherein the surface of the at least one flexure member is disengaged from the surface of the carrier when the at least one flexure member is in the second state.

6. The lancet device of claim 5, wherein the surface of the at least one flexure member is caused to move in a direction substantially parallel to a plane defined by the surface of the carrier when the at least one flexure member is caused to move between the first state and the second state.

7. The lancet device of claim 1, wherein the at least one flexure member flexes toward the housing upon contact with a camming surface to release the carrier from engagement with the at least one flexure member.

8. The lancet device of claim 7, wherein axial displacement of the shield into the housing causes the at least one flexure member to engage the camming surface and to release the at least one flexure member from the carrier.

9. A lancet device comprising:
a housing;
a shield at least partially disposed within the housing and movable with respect thereto;
a carrier having a puncture element and a first engagement surface, the carrier being movable between a first position where a distal end of the puncture element is disposed within the shield, and a second position where the distal end of the puncture element is exposed from the shield;
a flexural element having a second engagement surface, the flexural element transitionable between a first state, in which the first engagement surface is engaged with the second engagement surface, and a second state, in which the first engagement surface is not engaged with the second engagement surface; and
a drive spring disposed within the housing and in contact with a portion of the carrier for biasing the carrier towards the second position when the flexural element is in the second state,
wherein the flexural element is transitioned from the first state to the second state by a portion of the shield contacting a portion of the flexural element thereby moving the flexural element radially outward.

10. The lancet device of claim 9, wherein the flexural element is generally annular.

11. The lancet device of claim 9, wherein the second engagement surface is caused to move in a direction substantially parallel to a plane defined by the first engagement surface when the flexural element is caused to move between the first state and the second state.

12. The lancet device of claim 9, wherein the flexural element flexes toward the housing upon contact with a camming surface to release the carrier from engagement with the flexural element.

13. The lancet device of claim 12, wherein axial displacement of the shield into the housing causes the flexural element to engage the camming surface and to release the flexural element from the carrier.

14. A lancet device comprising:
a housing;
a shield disposed within the housing, the shield and housing being movable with respect to each other;
a lancet assembly disposed within the housing and comprising a movable carrier and a skin puncturing element having a sharpened tip adapted for puncturing the skin of a patient, the carrier movable between a first position where the sharpened tip is disposed within the shield, and a second position where the skin puncturing element is exposed from the shield;
at least one flexure member transitionable between a first state, in which it engages a portion of the carrier to maintain the carrier in the first position, and a second state in which it does not engage the portion of the carrier and the carrier is able to move to the second position; and
a drive spring disposed within the housing and in contact with a portion of the carrier for biasing the carrier towards the second position when the at least one flexure member is in the second state,
wherein the at least one flexure member is transitioned from the first state to the second state by a portion of the shield contacting a portion of the at least one flexure member thereby moving the at least one flexure member radially outward.

15. The lancet device of claim 14, wherein the drive spring comprises a coil spring positioned between a surface of the housing and the lancet assembly.

16. The lancet device of claim 14, wherein the at least one flexure member is generally annular.

17. The lancet device of claim 14, wherein a surface of the at least one flexure member is caused to move in a direction substantially parallel to a plane defined by a surface of the carrier when the at least one flexure member is caused to move between the first state and the second state.

18. The lancet device of claim 14, wherein the at least one flexure member may be caused to change from the first state to the second state upon movement of the shield into the housing.

19. The lancet device of claim 18, wherein movement of the shield into the housing causes the at least one flexure member to engage a camming surface which forces the at least one flexure member to expand in an outward direction and release a carrier latch from cooperation with the carrier.

20. The lancet device of claim 14, further comprising a retraction spring to bias the carrier toward the first position.

21. A medical device comprising:
a carrier comprising a puncture element;
a housing;
a shield internally movable with respect to said housing; and
a drive spring disposed within the housing and in contact with a portion of the carrier,
wherein said housing comprises a distally extending flexural element extending from a proximal end of the housing, said flexural element comprises a carrier latch,
wherein the shield comprises a proximally extending cam to engage said flexural element,
wherein the carrier comprises a surface for releasably cooperating with said carrier latch, and
wherein movement of said shield internally to said housing causes the cam of the shield to contact a portion of said flexural element to move the flexural element radially outward and release said carrier latch from cooperation with said carrier.

22. The medical device of claim 21, wherein said cam substantially resists flexure during engagement with said flexural element.

* * * * *